US010519770B2

(12) United States Patent
Chen et al.

(10) Patent No.: US 10,519,770 B2
(45) Date of Patent: Dec. 31, 2019

(54) CALIBRATION MODULE FOR POOLED OPTICAL SENSORS IN DOWNHOLE FLUID ANALYSIS

(71) Applicant: HALLIBURTON ENERGY SERVICES, INC., Houston, TX (US)

(72) Inventors: Dingding Chen, Tomball, TX (US); Christopher M. Jones, Houston, TX (US); Bin Dai, Spring, TX (US); Darren Gascooke, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 364 days.

(21) Appl. No.: 15/514,469

(22) PCT Filed: Mar. 22, 2016

(86) PCT No.: PCT/US2016/023642
§ 371 (c)(1),
(2) Date: Mar. 24, 2017

(87) PCT Pub. No.: WO2017/164854
PCT Pub. Date: Sep. 28, 2017

(65) Prior Publication Data
US 2018/0171787 A1  Jun. 21, 2018

(51) Int. Cl.
*E21B 49/08* (2006.01)
*E21B 43/12* (2006.01)
(Continued)

(52) U.S. Cl.
CPC ............ *E21B 49/08* (2013.01); *E21B 43/121* (2013.01); *E21B 44/00* (2013.01); *G01N 21/85* (2013.01);
(Continued)

(58) Field of Classification Search
None
See application file for complete search history.

(56) References Cited

U.S. PATENT DOCUMENTS 7,398,159 B2 * 7/2008 Venkataramanan .. E21B 49/005
702/11
7,966,273 B2 * 6/2011 Hegeman ................. G06N 3/02
706/17
(Continued)

FOREIGN PATENT DOCUMENTS

WO   WO-2015/112177 A1   7/2015

OTHER PUBLICATIONS

International Search Report and Written Opinion from PCT/US2016/023642, dated Nov. 28, 2016.

*Primary Examiner* — Suzanne Lo
(74) *Attorney, Agent, or Firm* — Gilliam IP PLLC

(57) ABSTRACT

A method including selecting candidate sensors for pooled calibration and determining a multivariate fluid characterization model with the pooled sensors is provided. The method includes determining a virtual master kernel standardization model with the pooled sensors, implementing a calibration result into a processor circuit and determining a value of a fluid characteristic by applying the multivariate fluid composition model to a plurality of responses obtained from a plurality of sensor responses to the fluid sample. The plurality of responses may be obtained from the plurality of sensor responses using the virtual master kernel standardization model. The method includes optimizing a wellbore operation based on the value of the fluid characteristic. A device for implementing the above method is also provided.

16 Claims, 10 Drawing Sheets

(51) Int. Cl.
*E21B 44/00* (2006.01)
*G01N 21/85* (2006.01)
*G06N 3/08* (2006.01)
*G06N 3/10* (2006.01)

(52) U.S. Cl.
CPC ............... *G06N 3/086* (2013.01); *G06N 3/10* (2013.01); *E21B 2049/085* (2013.01)

(56) References Cited

U.S. PATENT DOCUMENTS

| | | |
|---|---|---|
| 9,347,314 B2 * | 5/2016 | Indo ..................... E21B 49/088 |
| 2014/0306096 A1 | 10/2014 | Freese et al. |
| 2014/0324366 A1 | 10/2014 | Ljungdahl et al. |
| 2015/0247950 A1 | 9/2015 | Perkins |
| 2015/0300945 A1 * | 10/2015 | Gao ..................... G01N 21/274 |
| | | 702/104 |
| 2015/0330215 A1 | 11/2015 | Jamison et al. |

* cited by examiner

CALIBRATION MODULE FOR POOLED OPTICAL SENSORS IN DOWNHOLE FLUID ANALYSIS

BACKGROUND

Real-time formation fluid analysis using fluid characterization models with synthetic optical sensor inputs is sensitive to the quality of sensor data transformation from the downhole tool parameter space to the synthetic parameter space, and to the quality of multivariate input selection. In common practice, each sensor has its own sensor-based fluid characterization models and cross-space data transformation models. While fluid characterization models are calibrated in a synthetic database using virtual sensor responses on a large collection of global oil and fluid samples with known properties, cross-space data transformation models are usually trained on a small number of reference fluids with measured sensor responses as calibration inputs and simulated virtual sensor responses as calibration outputs.

In formation sampling and testing, data from a downhole optical sensor are routinely converted to variable inputs of fluid characterization models through cross-space data mapping. However, quality related issues on fluid property estimation might arise because of the narrow dynamic range of optical signals used with sensor-based calibration, and the limitation of applying data transformation algorithms derived from a small number of reference fluids to a larger number of formation fluids having greater variety and complexity. Uncertainty in cross-space data mapping reduces the compatibility of transformed data with calibration data in virtual sensor parameter space, and could result in non-negligible prediction error on fluid answer products. The disagreement of input selection with sensor-based nonlinear calibration on each fluid predictive model may also produce inconsistent output from the sensors on the same tool or different tools when tested on the same fluids, making real-time signal processing and data interpretation difficult.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

In the figures, elements having the same or similar reference numeral have the same or similar functionality and description, unless stated otherwise.

DETAILED DESCRIPTION

Figure 1:
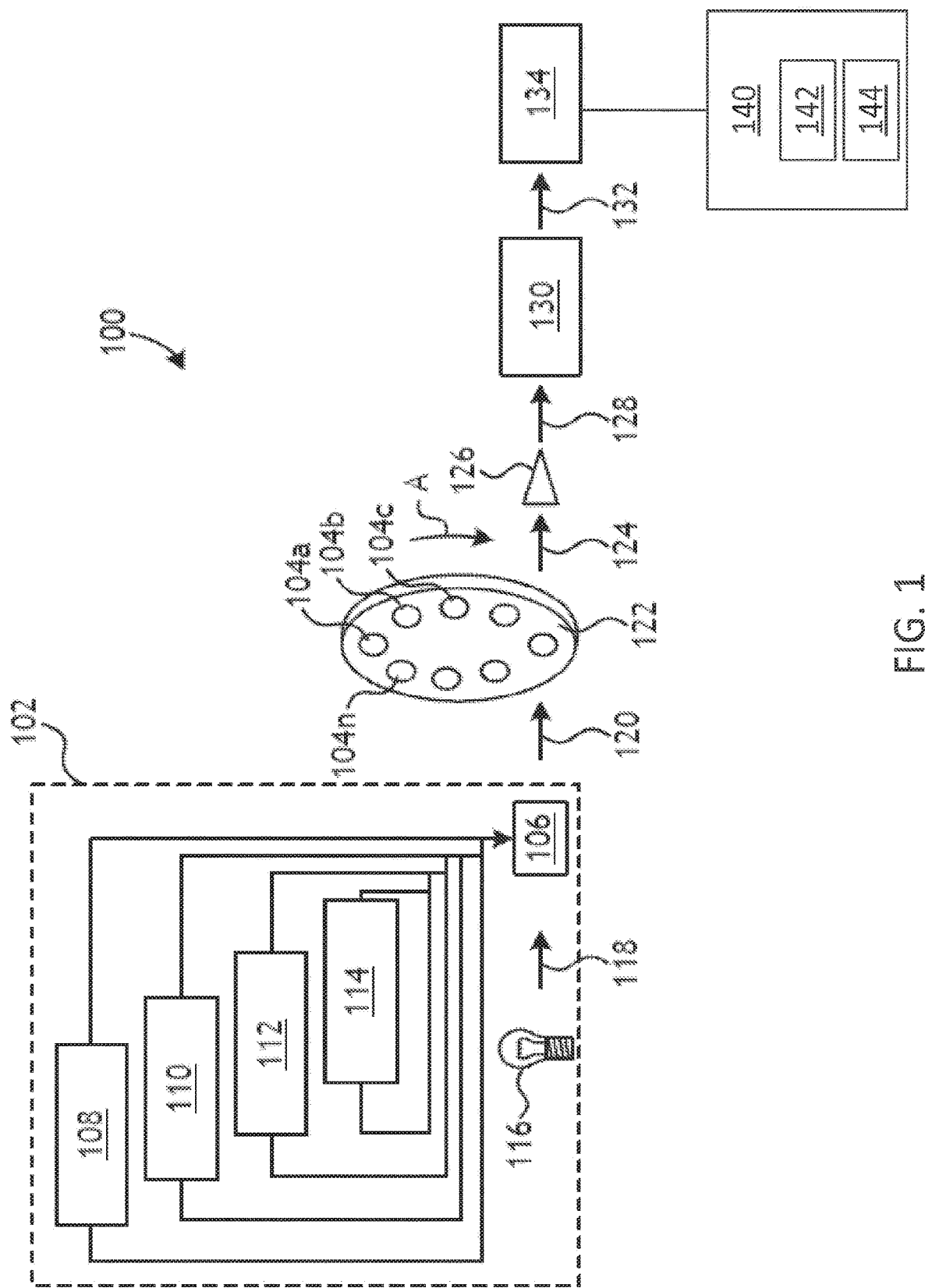
FIG. 1 illustrates a calibration system used to calibrate an optical sensor.

The present disclosure relates to calibration and data processing of optical sensors for downhole optical fluid analysis. More specifically, the present disclosure provides a calibration module that can be applied to pooled optical sensors for downhole fluid analysis.

According to one or more embodiments, a method including selecting candidate optical sensors for pooled calibration in ruggedizing data transformation and downhole fluid characterization is provided. The method includes determining a multivariate fluid characterization model and a virtual master kernel standardization model through pooled calibration with the same or different sensors, implementing a calibration result into a processor circuit and determining a value of a fluid characteristic by applying the shared multivariate fluid composition model to a plurality of synthetic responses obtained from a plurality of downhole sensor responses to the fluid sample. The plurality of synthetic responses may be obtained from the plurality of sensor responses using the shared virtual master kernel standardization model. The method includes optimizing a wellbore operation based on the value of the fluid characteristic. A device for implementing the above method is also provided.

The present disclosure provides methods and systems for downhole fluid analysis using a novel calibration module for pooled optical sensors. Embodiments disclosed herein tolerate the inherent uncertainty of cross-space transformation and multivariate input selection in multivariate fluid analysis while providing a reliable value for a fluid characteristic or property. Calibration modules according to the present disclosure are capable of providing a controllable calibration environment for tackling the inherent variation of sensing element fabrication and optical spectral measurements. Accordingly, calibration modules described herein provide fluid predictive models that are robust with respect to imperfect cross-space transformations. Embodiments consistent with the present disclosure also include enhanced machine learning that make candidate fluid model inputs more consistent or less dependent on initial conditions for nonlinear training. Calibration modules as disclosed herein include fluid predictive algorithms and optical data transformation algorithms shared among a plurality of sensors selected from the same wellbore tool or different wellbore tools. Thus, embodiments as disclosed herein improve measurement consistency for the plurality of sensors when tested on the same fluids and under similar environmental conditions.

An optical sensor as disclosed herein may include at least one or more sensing elements. In some embodiments, at least one of the sensing elements is an integrated computational element (ICE) designed to measure a fluid characteristic or property. According to some embodiments, an ICE is essentially an optical interference-based device that can be designed to operate over a continuum of wavelengths in the electromagnetic spectrum from the UV to mid-infrared (MIR) ranges, or any sub-set of that region. Electromagnetic radiation that optically interacts with a substance is changed and processed by the ICE so as to be readable by a detector, such that an output of the detector can be correlated to the physical or chemical property of the substance being analyzed. Other examples of sensing elements and optical system components may include band-pass filters, notch filters, neutral density filters, beam-splitters, polarizing beamsplitters, prisms, diffraction gratings, Fresnel lenses, and the like.

An ICE may include a plurality of optical layers consisting of various materials whose index of refraction and size (e.g., thickness) may vary between each layer. An ICE design refers to the number and thickness of the respective layers of the ICE. The layers may be strategically deposited and sized to selectively pass predetermined fractions of electromagnetic radiation at different wavelengths configured to substantially mimic a regression vector corresponding to a particular physical or chemical property of interest of a substance. Accordingly, an ICE design will exhibit a transmission function that is weighted with respect to wavelength. As a result, the output light intensity from the ICE conveyed to a detector may be related to the physical or chemical property of interest for the substance.

Calibration modules as disclosed herein include pools of optical sensors having the same or similar multi-element configuration, and sharing at least one ICE having the same or similar component design. Without limitation, some of the ICE designs used as sensing elements in optical sensors as disclosed herein may include a methane ICE (designed to measure methane concentration), a water ICE (designed to measure water concentration), or a gas-oil-ratio (GOR) ICE (designed to measure GOR in a fluid), or an aromatics (ARO) ICE (designed to measure ARO concentration), among others. In some embodiments, a pooled calibration module includes calibrating fluid models for estimating fluid compositions and properties in the synthetic parameter space of the pooled sensors. Additionally, the calibration module may include a calibrating instrument standardization algorithm to make optical data transformation from the real operational sensor responses to virtual synthetic sensor responses of a sample fluid.

The terms "optical computing device" and "optical sensor" are used herein interchangeably and refer generally to a sensor configured to receive an input of electromagnetic radiation that has interacted with a substance and produced an output of electromagnetic radiation from a sensing element arranged within or otherwise forming part of the optical computing device. The sensing element may be, for example, an ICE as described above. Prior to field use, the optical computing device, with each sensing element employed therein, is calibrated such that each output response can be used in conjunction with others to calculate fluid composition and properties through various signal transformation and characterization models upon being exposed to downhole conditions. When an optical computing device is not properly calibrated, the resulting models or algorithms, which correlate optical sensor responses to the fluid characteristics of interest, may not be able to provide accurate fluid predictions upon deployment.

After manufacture and before downhole use, each optical computing device is carefully calibrated against known reference fluids for temperature and pressure ranges expected to be encountered in the field. The measurement data of each sensing element on the given reference fluids form the basis for developing optical signal transformation models. Once selected reference fluids adequately possess representative features of global petroleum and/or formation fluids, the optical signal transformation algorithms calibrated with a variety of structures can be found for a wide range of applications in processing downhole optical tool data.

Formation fluid analysis uses field sensor measurements obtained from downhole fluid sampling. Accordingly, factors that may have strong impact on the quality of fluid prediction (e.g., fluid composition and fluid characteristics) include variations in downhole fluid pumping rate, a transient status in the flow line, tool vibrations, firmware changes, the condition of sensing elements, fluid contamination level, and other testing conditions. Fluid predictive model calibration modules as disclosed herein provide a robust real-time fluid prediction with respect to the above factors. This may be particularly desirable when a new sensor is deployed for the first time.

FIG. 1 illustrates an exemplary calibration system 100 that may be used to calibrate one or more sensing elements used in an optical sensor. As illustrated, system 100 may include a measurement system 102 in optical communication with one or more sensing elements 104 (shown as 104a, 104b, 104c . . . 104n) that are to be calibrated. Each sensing element 104a-n may include, without limitation, an optical band-pass filter or a multivariate sensing element/integrated computational element (e.g., an ICE). Measurement system 102 may circulate one or more reference fluids with different chemical compositions and properties (i.e., methane concentration, aromatics concentration, saturates concentration, GOR, and the like) through an optic cell 106 over widely varying calibration conditions of temperature, pressure, and density. Thus, optical transmission and/or reflection measurements of each reference fluid in conjunction with each sensing elements 104a-n may be made at such conditions.

Measurement system 102 may comprise an optical pressure-volume-temperature (PVT) instrument, and the reference fluids circulated in the measurement system 102 may include representative fluids commonly encountered in downhole applications. System 100 may collect output signals from each sensing element 104a-n for each specified reference fluid at varying calibration conditions. In some cases, the reference fluids may include representative fluids that are easy to operate for manufacturing calibration such as: dodecane, nitrogen, water, toluene, 1-5 pentanediol, and two liquid crude oils or fluids with no gas concentration (e.g., dead oil). The crude reservoir oils used as reference fluids may be, for example, global oil library 13 (or "GOL13"), and global oil library 33 (or "GOL33"). In other cases, the reference fluids may include samples of live oils mixed with dead oil and hydrocarbon gas, such as methane, for example, and the samples of hydrocarbon gases and/or $CO_2$.

Measurement system 102 may vary each reference fluid over several set points spanning varying calibration conditions. To accomplish this, as illustrated, measurement system 102 may include a liquid charging system 108, a gas charging system 110, a temperature control system 112, and a pressure control system 114. The liquid charging system 108 injects reference fluids into the fluid circuit to introduce fluid varying perturbations such that calibrating the sensing elements 104a-n will incorporate all the expected compounds found in the particular reference fluid. The gas charging system 110 may inject known gases (e.g., $N_2$, $CO_2$, $H_2S$, methane, propane, ethane, butane, combinations thereof, and the like) into the circulating reference fluids. The temperature control system 112 may vary the temperature of the reference fluid to simulate several temperature set points that the sensing elements 104*a-n* may encounter downhole. Lastly, the pressure control system 114 may vary the pressure of the reference fluid to simulate several pressure set points that the sensing elements 104*a-n* may encounter downhole.

Optic cell 106 is fluidly coupled to each system 108, 110, 112, and 114 to allow the reference fluids to flow therethrough and recirculate back to each of the systems 108, 110, 112, and 114 in a continuous, closed-loop fluid circuit. While the reference fluid circulates through optic cell 106, a light source 116 emits electromagnetic radiation 118 that passes through optic cell 106 and the reference fluid flowing therethrough. As the electromagnetic radiation 118 passes through the optic cell 106 it optically interacts with the reference fluid and generates sample interacted light 120, which includes spectral data for the particular reference fluid circulating through the measurement system 102 at the given calibration conditions or set points. The sample interacted light 120 may be directed toward sensing elements 104*a-n*, which, as illustrated, may be arranged or otherwise disposed on a sensing platform 122. Sensing elements 104*a-n* receive sample interacted light 120 and generate a computation light 124 that is measured by a detector 126.

Sensing platform 122 is configured to provide at least a portion of sample interacted light 120 having similar optical properties to each of the plurality of sensing elements 104*a-n*. In some embodiments, sensing platform 122 provides the same portion of sample interacted light 120 to the plurality of sensing elements 104*a-n* in a known time sequence. In some embodiments, sensing platform 122 includes a sensor wheel configured to rotate in the direction A, about an axis parallel to the impinging sample interacted light 120. While shown as arranged in a single ring on sensing platform 122, sensing elements 104*a-n* may alternatively be arranged in two or more rings on the sensing platform 122. Once calibrated, according to embodiments disclosed herein, sensing elements 104*a-n* mounted on sensing platform 122 may be included in a downhole tool for measurement of a fluid characteristic.

During calibration, sensing platform 122 may be rotated at a predetermined frequency such that each sensing element 104*a-n* may optically interact with the sample interacted light 120 for a brief period and sequentially produce optically interacted light 124 that is conveyed to detector 126. Detector 126 may be generally characterized as an optical transducer and may comprise, but is not limited to, a thermal detector (e.g., a thermopile), a photo-acoustic detector, a semiconductor detector, a piezo-electric detector, a charge coupled device (CCD) detector, a video or array detector, a split detector, a photon detector (e.g., a photomultiplier tube), photodiodes, and any combination thereof. Upon receiving individually-detected beams of computation light 124 from each sensing element 104*a-n*, detector 126 may generate or otherwise convey corresponding response signals 128 to a data acquisition system 130. A data acquisition system 130 may time multiplex each response signal 128 received from the detector 126 corresponding to each sensing element 104*a-n*. A corresponding set of resulting output signals 132 is generated and conveyed to a data analysis system 134, for processing and providing input parameters for various fluid predictive models. The fluid predictive models use outputs from each sensing element 104*a-n* as candidate variables.

Data analysis system 134 may be coupled to a computer 140, which may include a memory 142 and a processor 144. Memory 142 may store commands which, when executed by processor 144, cause computer 140 to perform at least some of the steps in the methods described herein and otherwise consistent with the present disclosure. For example, in embodiments consistent with the present disclosure, models and algorithms for data processing and fluid computation models as disclosed herein may be implemented into processor 144.

Once sensing platform 122 is calibrated, one or more calibrated sensing platforms 122 may then be installed on a downhole tool with other system components, for assembly validation testing. To validate the optical response of the sensor assembly, the sensor may be placed in an oven that regulates the ambient temperature and pressure. The reference fluids used to calibrate sensing platform 122 may be selectively circulated through the optical sensor at similar set points used to calibrate the sensing elements 104*a-n*. More particularly, the reference fluids may be circulated through the optical sensor at various set point downhole conditions (i.e., elevated pressures and temperatures) to obtain measured optical responses.

Sensing elements 104*a-n* are calibrated using the response of the sensors to reference fluids in a tool parameter space. On the other hand, fluid spectroscopic analysis and fluid predictive model calibration using a large amount of data in a standard oil library is performed in a synthetic parameter space (alternately referred to as Optical-PVT data space). Synthetic sensor responses for each sensor in the downhole tool are calculated as a dot product of full-wavelength-range of fluid spectrometry and sensor element spectrum excited by a light source. The value of the dot product may vary nonlinearly or linearly compared to the actual sensor response due to the difference between the mathematical approximation used in calculating synthetic sensor response and the real system implementation. To compensate for the difference above, the measurement data from the sensors in the downhole tool can be transformed from the tool parameter space to the synthetic parameter space through a reverse transformation algorithm before applying fluid predictive models. In some embodiments, fluid predictive models are calibrated with different synthetic optical inputs, and saved as candidate models in an optical fluid model base. This provides sufficient adaptability in dealing with data transformation uncertainty and improves the formation fluid compositional analysis and field data interpretation.

Figure 2:
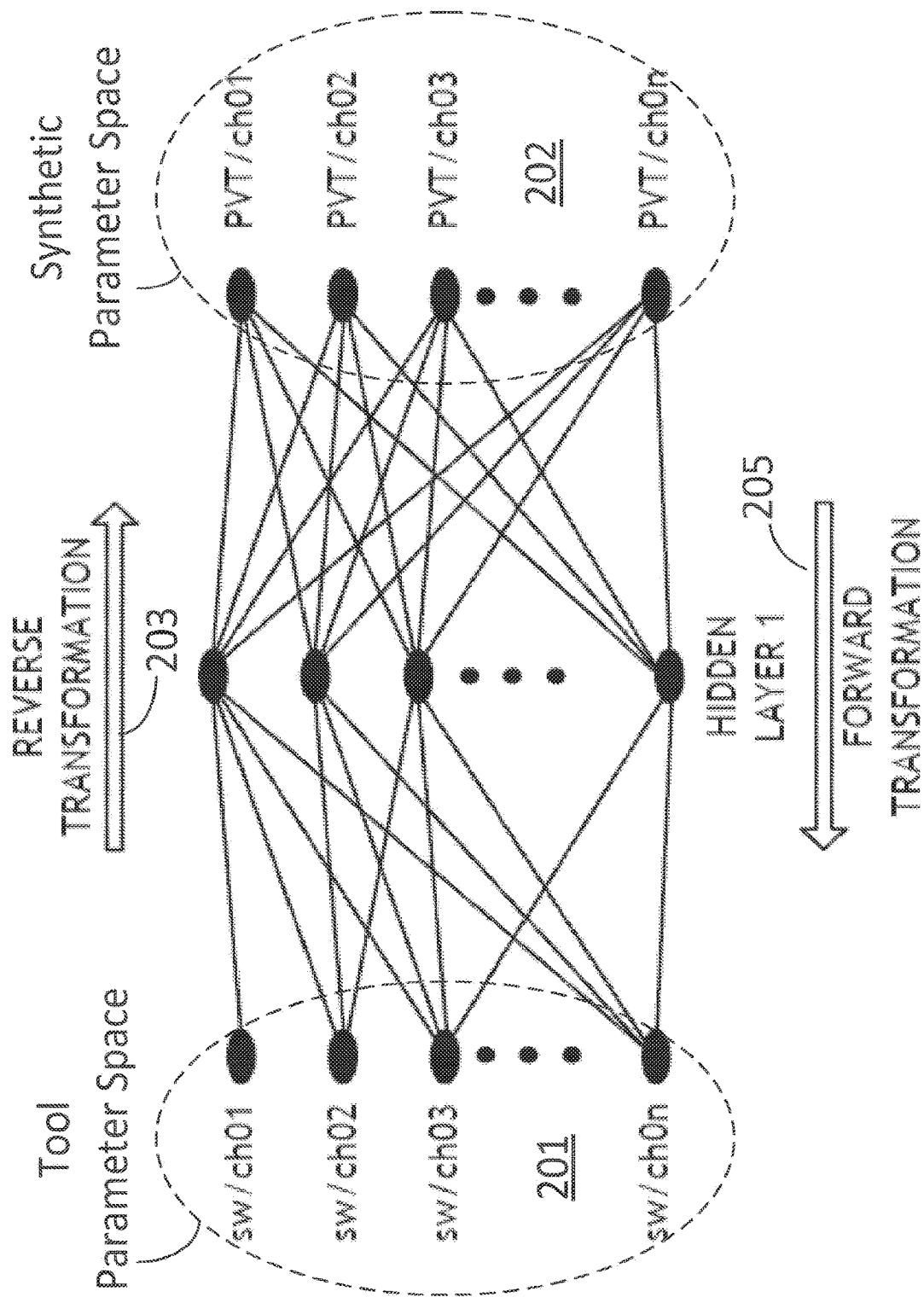
FIG. 2 illustrates a general transformation model framework applied to a forward transformation and a reverse transformation between a tool parameter space and a synthetic parameter space with neural networks.

In current practice, an optical fluid model is dependent on the downhole tool used for measurement and includes data transformation (i.e., standardization) models and property predictive models. To provide adequate flexibility for optical data processing and interpretation, an optical fluid model includes the following candidate constituents: transformation models calibrated on selected reference fluids through reverse transformation, transformation models calibrated on selected reference fluids through forward transformation, and predictive models calibrated on both Optical-PVT database and sensing platform 122 data spaces. Depending on the data space in which the fluid property predictive models are calibrated, data transformation models convert measured or simulated optical sensor output between a tool parameter space and a synthetic parameter space. FIG. 2 illustrates one such transformation.

FIG. 2 illustrates an embodiment of a general transformation model framework including a forward transformation 205 and a reverse transformation 203 between data in a tool parameter space 201 and a synthetic parameter space 202 with a non-linear algorithm. In some embodiments, the non-linear algorithm used to implement reverse transformation 203 is a neural network model. In some embodiments, the forward 205 or reverse 203 transformation includes a multi-input, multi-output neural network that may be applied by data analysis system 134 of FIG. 1 to receive inputs and generate outputs of sensing element responses. The model that converts the actual sensing element responses (SW/Ch01-Ch0n) from tool parameter space 201 to synthetic parameter space 202 (PVT/Ch01-Ch0n) is reverse transformation 203. The model that converts data from synthetic parameter space 202 into tool parameter space 201 is forward transformation 205. Although the illustrated general transformation model framework in FIG. 2 is configured with multi-input/multi-output non-linear neural networks, there is no limitation in using other non-linear and linear transformation algorithms with single-input/single-output and multi-input/single-output configurations.

Figure 3:
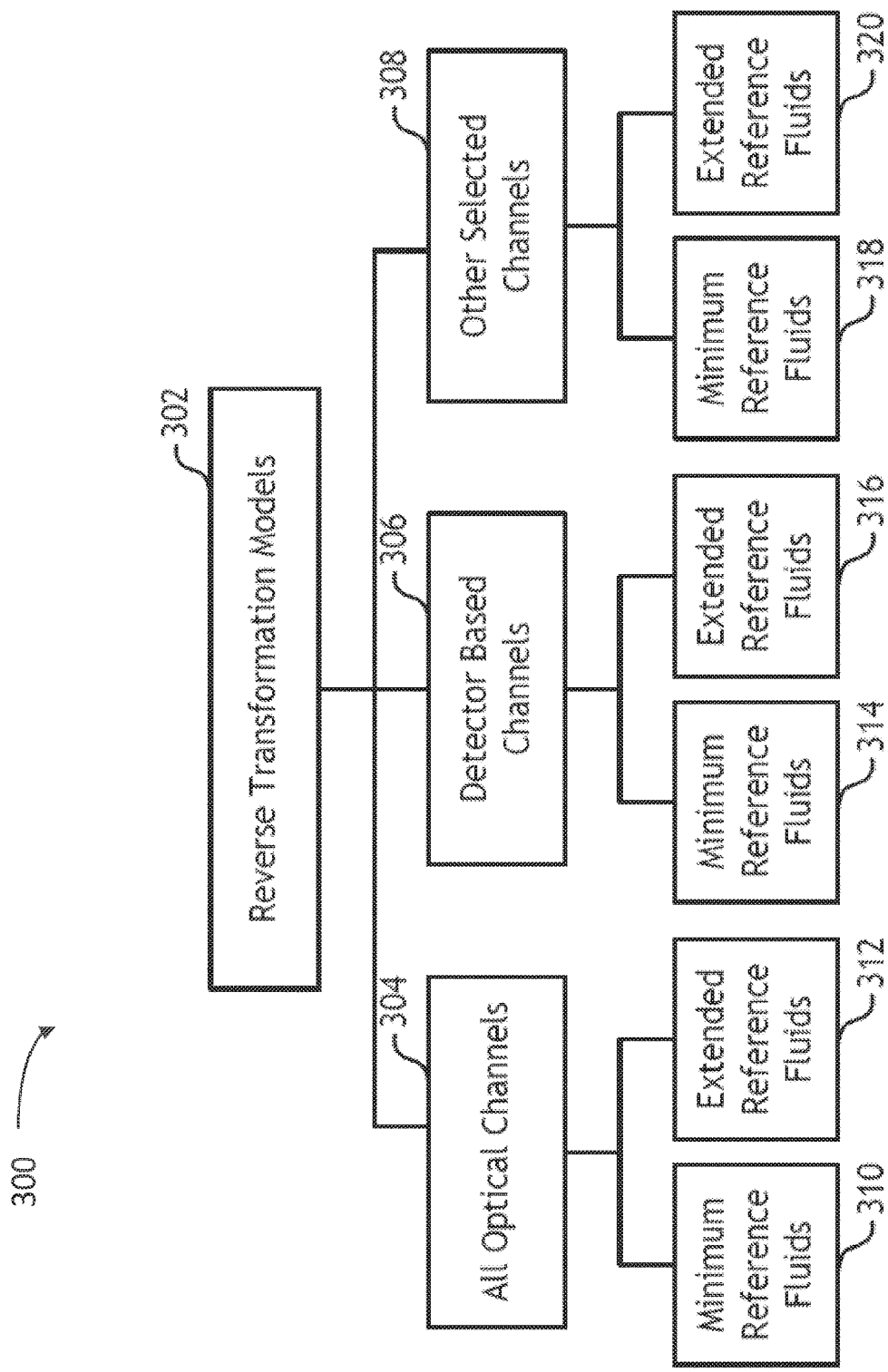
FIG. 3 depicts a hierarchical structure for reverse transformation models.

FIG. 3 illustrates an embodiment of a hierarchical structure for reverse transformation models 302. The variations of transformation models 302 may include converting all sensor responses 304 from each sensing element in a single model, converting the disjoined sensing elements in several detector-based models 306, or converting only selected sensor elements of interest 308 each time in different individual models. Compared to a single model implementation, multi-model options can improve the reliability of data construction in the output (i.e., transformed) parameter domain (e.g., synthetic parameter space 202, cf. FIG. 2) if one or more of the sensing elements (e.g., sensing elements 104a-n, cf. FIG. 1, and tool parameter space 201, cf. FIG. 2), as a transformation input, experience a problem. A plurality of reference fluid blocks 310-320, at the bottom of the hierarchical structure and coupled to the various sensors 304-308, represent the transformation models that can be built based on different reference fluids (e.g., minimum number of reference fluids 310, 314, 318 and extended reference fluids 312, 316, 320). The minimum number of reference fluids may refer to the seven representative fluids discussed above. These reference fluids are safe to use in a laboratory configuration and easy to clean for testing purposes. Sensing element responses on reference fluids (e.g., tool parameter space 201) generally benefit from a wide dynamic range as a representation of diverse samples in an existing Optical-PVT database and formation fluids. Extended reference fluids often include one or more fluids such as live oil, natural gas and/or gas condensate to provide a more robust transformation model.

In some embodiments, reverse transformation 203 (FIG. 2) converts sensor measurements from tool parameter space 201 into synthetic parameter space 202 prior to applying fluid characterization models. Accordingly, fluid characterization models use synthetic sensing element responses 202 as input to calculate fluid composition and physical properties. Forward transformation 205 (FIG. 2) can be used to convert a whole set of simulated sensing element responses from synthetic parameter space 202 to tool parameter space 201 prior to developing predictive models in tool parameter space 201. As seen in FIG. 2, forward transformation 205 can be created by switching the input and the output of a neural network model. In other words, using a synthetic-sensor response as an input and a measured sensor response as an output a neural network can then be trained to calibrate forward transformation algorithms.

As will be appreciated, a hierarchical structure for the reverse transformation models 302, as illustrated in FIG. 3, can also be applied to forward transformation models. After forward transformation 205 is developed, it can be used to convert the synthetic sensor responses of the global samples in synthetic parameter space 202 into tool parameter space 201. Then the fluid property predictive models can be calibrated in tool parameter space 201, and the further transformation is not needed in field data processing because measured optical responses from the sensor can be used as model inputs directly for fluid compositional analysis. Compared to the reverse transformation, which applies on-line sensor data conversion each time before making a fluid prediction, forward transformation usually only applies one time off-line to convert synthetic sensor responses for fluid prediction model development. However, reverse and forward transformations have different complexity with neural network implementation. Compared to a reverse transformation, a forward transformation typically uses a larger number of reference fluids for calibration, and consequently may induce higher uncertainty in fluid model development with use of transformed synthetic database. Therefore, reverse transformation is selected hereafter as general framework for cross-space transformation and used in conjunction with cross-tool transformation described below for operational fluid model validation.

Figure 4:
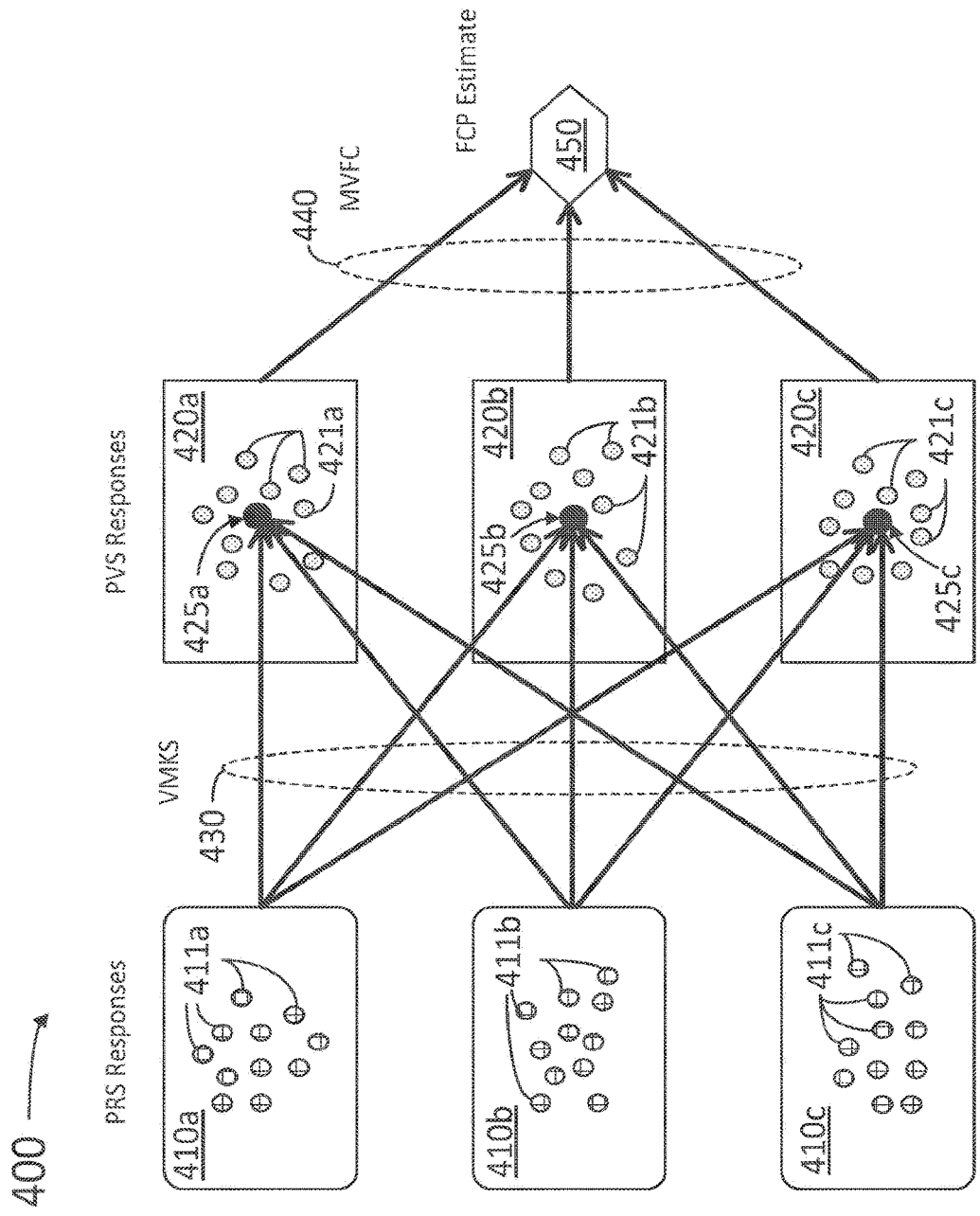
FIG. 4 depicts a block diagram illustrating the operation of a calibration module applied to a pool of optical sensors.

FIG. 4 depicts a block diagram illustrating the operation of a calibration module 400 as applied to a plurality of sensing elements from a pool of optical sensors. Blocks 410a, 410b and 410c represent pooled real sensor (PRS) responses 411a, 411b, and 411c (hereinafter collectively referred to as 'PRS responses 411') from three (3) sensing elements a, b, and c. For example, a collection of sensing elements 104a, 104b, and so on, from multiple sensor wheels in sensing platform 122 (cf. FIG. 1) corresponds to PRS block 410a, PRS block 410b, and so on. More specifically, in some embodiments, PRS block 410a may correspond to a number of methane ICEs in pooled calibration, PRS block 410b may correspond to a number of GOR ICEs, and PRS block 410c may correspond to a number of ARO ICEs. Each PRS response 411 corresponds to a specific sensing element response in tool parameter space within the selected pool of sensors.

Blocks 420a, 420b and 420c include pooled virtual sensor (PVS) responses 421a, 421b, and 421c, respectively (hereinafter referred to collectively as 'PVS responses 421' and 'PVS blocks 420'). Each PVS response 421 corresponds to a specific sensing element response in synthetic parameter space within the pool of optical sensors. Accordingly, FIG. 4 illustrates a pool of eleven (11) optical sensors selected in the calibration module. PRS responses 411 and PVS responses 421 illustrate the variation of optical responses of the three (3) sensing elements a, b, and c, within the selected pool of sensors. Within each PVS block 420, a kernel response 425a, 425b, and 425c (hereinafter collectively referred to as 'kernel responses 425') indicates the mean of the PVS responses 421 from the respective pooled sensors, for each sensing element. Accordingly, a virtual master sensor may be construed as a virtual sensor having kernel responses 425a, 425b, 425c, and so on, as synthetic parameter space values for each sensing element a, b, and c.

A fluid model to determine a fluid composition or property (FCP) 450 is built with a multivariate neural network fluid characterization algorithm (MVFC) 440 using optical responses in the synthetic parameter space from the pooled virtual sensors (PVS responses 421), including a kernel response based master sensor, as inputs. More generally, a calibration module as disclosed herein may include any number of candidate inputs from an optical sensor. For example, the calibration model may include a PVS block for simulated signal responses from different ICEs and other sensing elements. In some embodiments, a backward stepwise input selection is applied to pooled sensor data, and the top significant inputs are retained to the end of selection for optimizing a particular FCP prediction. In some embodiments the significant candidate elements from input selection correspond to the sensor channels (e.g., a, b, and c) having the most stable signal responses (i.e., for a given calibration database used). PVS responses 421 showing higher variance among the pooled sensors may be removed during the early stage of input selection. Thus, pooled calibration produces a robust MVFC 440 that perform better on new data using candidate inputs validated with the group of sensors.

A calibration module may include a virtual master kernel standardization (VMKS) algorithm 430 to produce a cross-space optical data reverse transformation converting PRS responses 411 to PVS responses 421 of the virtual master sensor. VMKS 430 may be a reverse transformation (e.g., reverse transformation 203, cf. FIG. 2) wherein the input data in the tool parameter space is selected from PRS responses 411, and the output data in the synthetic parameter space are kernel responses 425. VMKS 430 is built on the selected reference fluids using PRS responses as calibration inputs and kernel responses 425 as calibration outputs. In a field measurement, even if data transformation from the operational sensor to virtual master sensor may have outputs scattered or deviated from the ideal virtual master sensor responses to a certain degree, the likelihood of transformed multivariate data projected to a constrained area in the PVS parameter space would be high. In other words, the transformed data variation of a particular sensor may be within the range of training inputs of pooled sensors for fluid characterization, thereby allowing the candidate fluid models to provide a robust prediction on fluid compositions and properties.

A pooled cross-sensor transformation and pooled fluid model calibration principle improves the robustness of algorithm VMKS 430 and MVFC 440. Note that VMKS 430 and MVFC 440 are calibrated separately with different routines on different fluids in general. In some embodiments of calibration module 400, the pooled sensors in PRS blocks 410 and the pooled sensors in PVS blocks 420 may be the same. In other embodiments, however, pooled sensors in PRS blocks 410 may be different from pooled sensors in PVS blocks 420. Furthermore, the number of pooled sensors in PRS blocks 410 may be different from the number of pooled sensors in PVS blocks 420. In some embodiments, a large sensor pool is used in PVS blocks 420, wherein MVFC 440 includes a multi-input, single-output (MISO) neural network structure. On the other hand, VMKS 430 may include a multi-input, multi-output (MIMO) neural network structure.

The number of pooled optical sensors used to calibrate VMKS 430 may be smaller than the number of pooled sensors used to calibrate MVFC 440. For example, the availability of reference fluids and difference in setting temperatures and pressures during manufacturing calibration may constrain the size of data sets in PRS blocks 410. PRS responses 411 may include measurements from identical reference fluids using sensing elements from the same manufacturing batch. In some embodiments, the pool of sensors to calibrate VMKS 430 with PRS responses 411 is selected from a plurality of sensors to be installed on a given tool. In yet other embodiments, the pool of sensors with PRS responses 411 may be selected from sensors installed in different tools that will be deployed in the same geological region. This enhances robustness and consistency of VMKS 430 output in different application scenarios.

Calibration module 400 may include two inter-dependent sub-modules: one for determining MVFC 440, and one for determining VMKS 430 with output corresponding to the virtual master or kernel sensor responses represented by 425. A sub-module for determining MVFC 440 may include the virtual master sensor as one of the pooled sensors in calibrating FCP 450. Accordingly, the sub-module that generates VMKS 430 enables transformation of optical responses from multiple real sensors to the same kernel responses 425. On the other hand, MVFC 440 may determine the same FCP 450 using PVS responses 421 from multiple virtual sensors, including one master sensor generating kernel responses 425, suitably designed to mimic specific measurement conditions on diverse fluid samples. More generally, both VMKS 430 and MVFC 440 are subject to a multiple-to-one mapping rule, wherein multiple inputs are expected to give rise to the same, or very similar, output. In that regard, the multiplicity of inputs may arise due to sensing element variability, whereas the output is expected to be the same if the fluid measured is the same and under the same environmental conditions. Accordingly, mappings such as VMKS 430 or MVFC 440 are suitable to neural network implementation. In embodiments consistent with the present disclosure VMKS 430, MVFC 440, and FCP estimate 450 may be implemented in a processor circuit forming part of a computer in a data analysis system as disclosed herein (e.g., processor 144, computer 140, and data analysis system 134, cf. FIG. 1).

Figure 5:
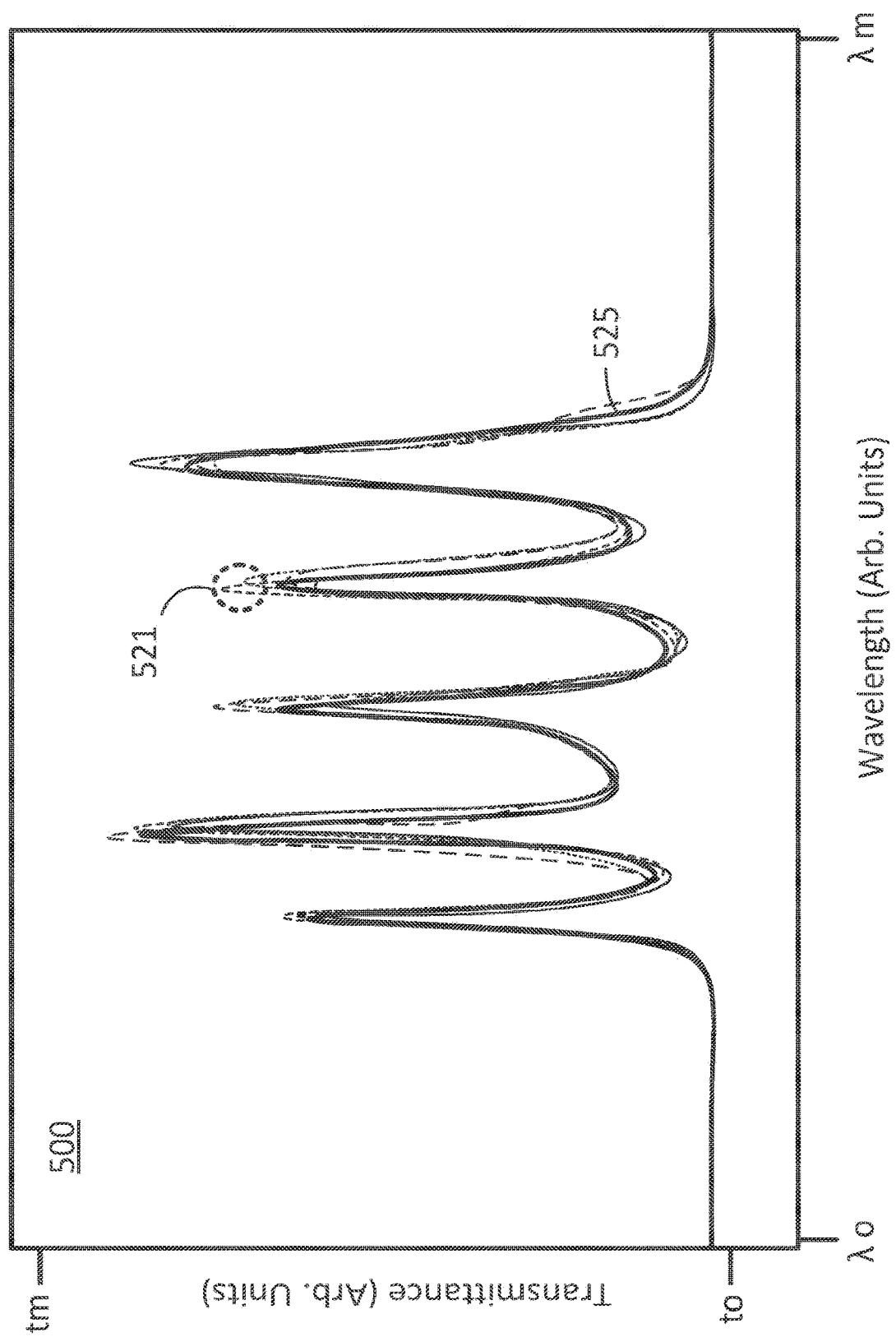
FIG. 5 depicts a chart illustrating the variation of transmittance spectra among sensing elements selected from a pool of optical sensors.

FIG. 5 depicts a chart 500 illustrating the variation of transmittance spectra 521 among sensing elements selected from a pool of optical sensors. The abscissae in chart 500 (X-axis) indicates wavelength (in arbitrary units), and the ordinates (Y-axis) indicates transmittance (in arbitrary units). While the specific range of wavelengths is not limiting, in some embodiments the wavelength range ($\lambda_o$, $\lambda_m$) is included in the near-infrared wavelength domain (NIR, from approximately 750 nm to approximately 2500 nm). In some embodiments, ($\lambda_o$, $\lambda_m$) is included in the ultraviolet-visible wavelength domain (UV-VIS, from approximately 250 nm to approximately 750 nm). Likewise, the transmittance range (to, tm) imposes no limitation to embodiments consistent with the present disclosure and may include any range between zero (0) and one (1).

The transmittance spectral data (e.g., spectra 521) of each pooled sensor element may be measured with a high-resolution laboratory instrument, for example, a UV-Vis (Ultraviolet-Visible) spectrometer or an NIR (near infrared) spectrometer spanning over the same wavelength range e.g., ($\lambda_o$, $\lambda_m$). The spectra shown in FIG. 5 could be the NIR spectra of an ICE from about 1100 to about 2700 nanometers. The wheel spectra with pooled sensor calibration may also include spectra measured in the visible and short-NIR color region (i.e., from about 300 to about 1100 nanometers), and MIR (medium infrared) region (i.e., from 2700 to 3500 nanometers).

The inconsistency of transmittance spectral measurements among curves of optical responses from pooled nominally identical elements 521 is one of the factors that introduces a spread in data points within each of PRS blocks 410 (FIG. 4) and PVS blocks 420 (FIG. 4). A kernel spectrum 525 is the mean of spectra 521, and is representative of a virtual sensor response (e.g., kernel responses 425, cf. FIG. 4).

The variation in transmittance spectra among the pooled sensing elements may reflect the fabrication tolerance and the inherent uncertainty in spectral measurement. Some variable features in spectra 521 may include the position and amplitude of a band peak value. Accordingly, the transmittance spectra 521 of each sensing element may be left or right shifted to some extent compared to kernel spectrum 525.

In embodiments of a calibration module consistent with the present disclosure, spectra 521 and kernel spectrum 525 are used in conjunction with PVT fluid spectroscopy data (not shown) to calculate training inputs for calibrating MVFC 440 (FIG. 4). Some embodiments use noisy training inputs (e.g., PVS responses 421, cf. FIG. 4) associated with measurement uncertainty to develop a ruggedized MVFC 440 with neural networks or other machine learning algorithms.

Figure 6:
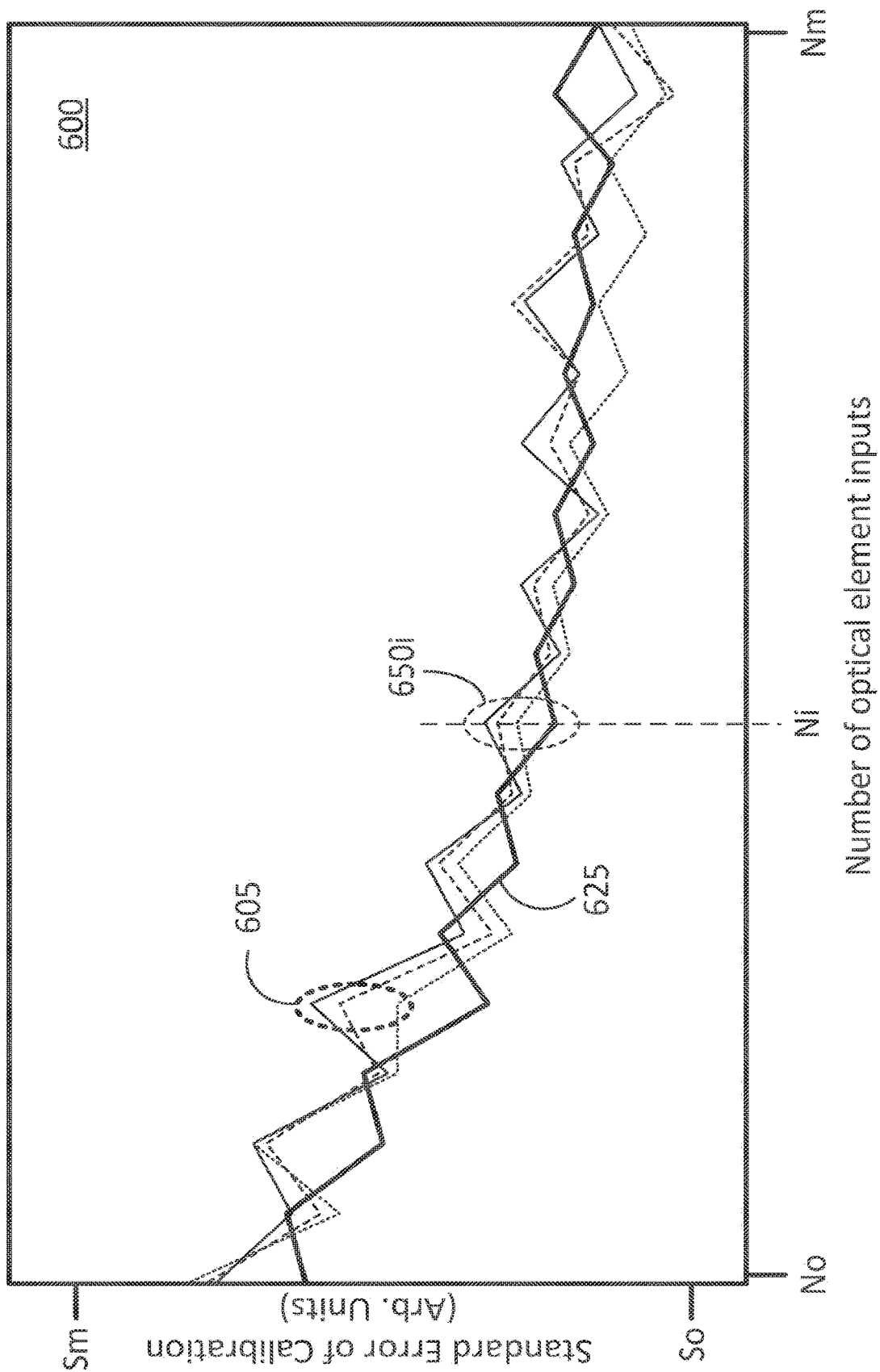
FIG. 6 depicts a chart illustrating the performance of a calibration module applied to a pool of optical sensors for downhole fluid analysis.

FIG. 6 depicts a chart 600 illustrating the performance of a calibration module applied to a pool of optical sensors for downhole fluid analysis, as disclosed herein. Without limitation, and for illustrative purposes only, FCP 450 (FIG. 4) in the calibration module illustrated in chart 600 is a methane concentration. The abscissae (X-axis) in chart 600 corresponds to the integral number of sensing element inputs used in the measurement. That is, for example, the number of sensing elements 104a-n in sensing platform 122 (cf. FIG. 1). While not limiting, the number of sensing elements may range from '$N_o$' approximately equal to four (4) to '$N_m$' approximately equal to twenty-five (25). The ordinates (Y-axis) in chart 600 correspond to a relative standard error of calibration (SEC), which is the root-of-mean-squared (RMS) error divided by the range of the target parameter (i.e., the actual methane concentration of the calibration fluid) in percent. The specific range of values ($S_o$, $S_m$) is not limiting, although it may include from '$S_o$' approximately equal to 2% or 3%, up to '$S_m$' approximately equal to 6% or 7%.

Each one of curves 605 represents the calibration performance of each sensor in the training pool for a different number of inputs. For example, with '$N_i$' sensing elements, each curve 605 has a value 650i for the SEC of methane concentration measurement, wherein the output of methane concentration of each sensor is obtained with the same MVFC calibration model applied to all sensors (e.g., MVFC 440, cf. FIG. 4). The optical element input of the MVFC for each sensor may be PVS responses calculated as the dot product of the fluid spectroscopy data and the transmittance spectrum of that particular element (e.g., PVS responses 421, cf. FIG. 4). Curve 625 is the calibration performance of a virtual master sensor obtained with the spectral mean for each sensing element of the pooled sensors (e.g., spectrum 525, cf. FIG. 5, and kernel responses 425, cf. FIG. 4).

Chart 600 demonstrates that an MVFC model built with pooled sensors including a virtual master sensor as disclosed herein reliably limits model performance as the best trade-off among calibrated individual sensors. Accordingly, when using MVFC 440 with a suitable VMKS 430 during an operation of formation sampling and testing, it may substantially reduce the uncertainty of real-time estimation of FCP 450 estimation from downhole optical sensor measurements.

Figure 7:
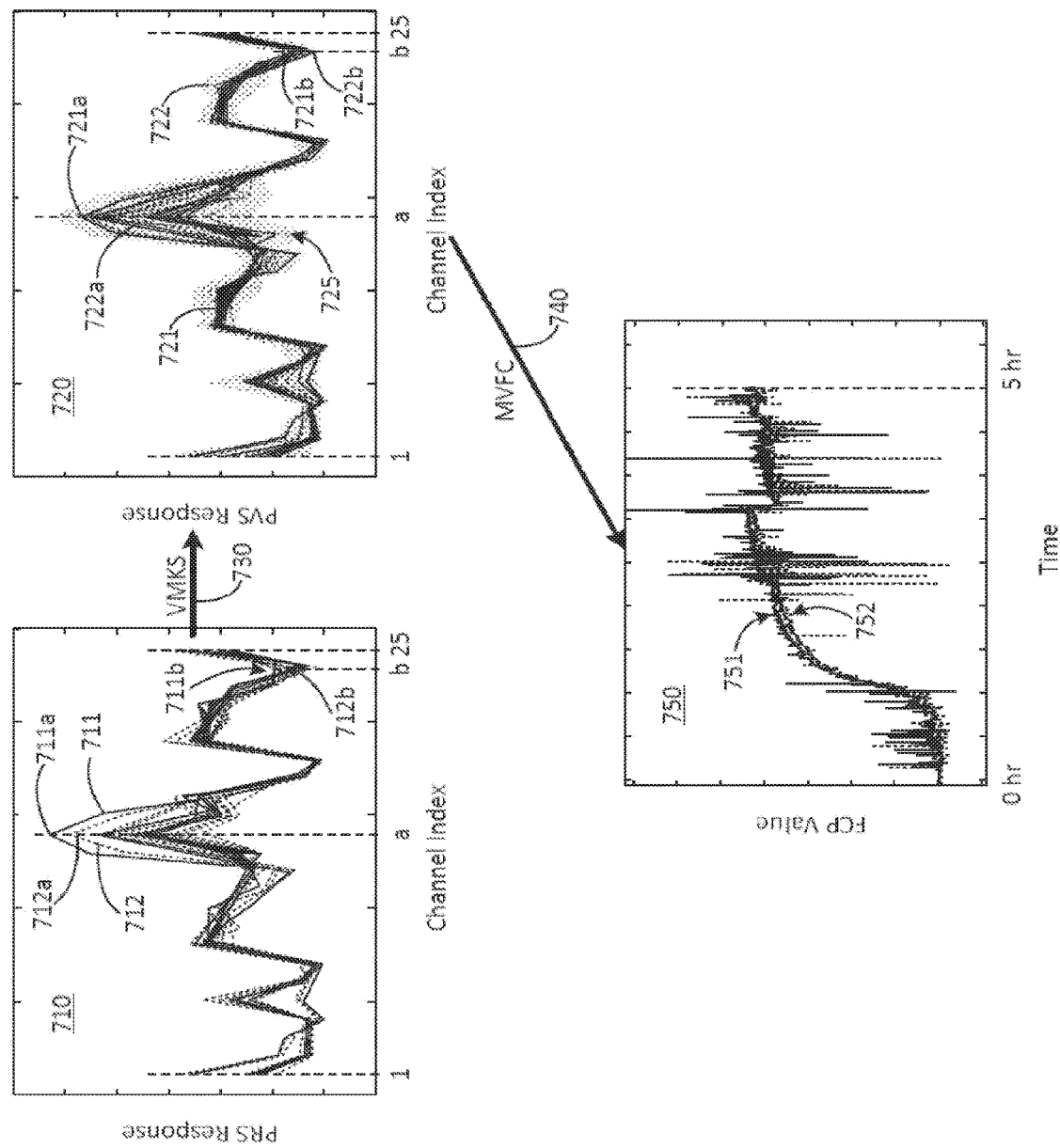
FIG. 7 illustrates the performance of a calibration module applied to a pool of optical sensors for a methane concentration measurement from a hydrocarbon extraction platform, over a five-hour data collection period.

FIG. 7 illustrates the performance of a calibration module applied to a pool of optical sensors for a methane concentration measurement from a hydrocarbon extraction platform, over a 5-hr fluid sampling period. In FIG. 7, charts 710, 720 and 750 present an optical tool data processing example using VMKS and MVFC models generated from the calibration module of pooled optical sensors (e.g. VMKS 430 and MVFC 440, cf. FIG. 4). The data in charts 710, 720 and 750 corresponds to a two-sensor tool (Sensor 1 and Sensor 2), each sensor having twenty five (25) sensing elements. At least some of the 25 sensing elements in Sensor 1 and Sensor 2 are ICEs for methane detection.

Chart 710 shows a PRS response 711 from Sensor 1 and the PRS response 712 from Sensor 2, during the 5-hr fluid sampling. PRS response 711 includes PRS responses from each of the 25 sensing elements in Sensor 1, including PRS responses 711a,b from sensing elements 'a' and 'b' in Sensor 1, respectively. Likewise, PRS response 712 includes PRS responses from each of the 25 sensing elements in Sensor 2, including PRS responses 712a,b from sensing elements 'a' and 'b' in Sensor 2, respectively.

Chart 720 shows a PVS response 721 from Sensor 1, and a PVS response 722 from Sensor 2. PVS responses 721 and 722 are transformed sensor responses from PRS responses 711 and 712, respectively, into synthetic parameter space. Accordingly, PVS response 721 and PVS response 722 are obtained using VMKS 730 as disclosed herein (e.g., VMKS 430, cf. FIG. 4). PVS response 721 includes PVS responses from each of the 25 sensing elements in Sensor 1, including PVS responses 721a,b from sensing elements 'a' and 'b' in Sensor 1, respectively. Likewise, PVS response 722 includes PVS responses from each of the 25 sensing elements in Sensor 2, including PVS responses 722a,b from sensing elements 'a' and 'b' in Sensor 2, respectively. PVS responses 721 and 722 are well constrained in the synthetic parameter calibration space of PVS responses 725. The agreement between PVS responses 721 and 722 within the limits of 725 indicates that Sensor 1 and Sensor 2 function properly, and are consistent with principles of a VMKS model as disclosed herein.

Chart 750 provides FCP values in curves 751 and 752 from Sensor 1 and Sensor 2, respectively. Specifically, but without limitation, the FCP value in chart 750 (Y-axis) corresponds to a Methane (C1) concentration over the 5-hr fluid sampling period. More generally, curves 751 and 752 correspond to an FCP obtained using MVFC 740 as disclosed herein (e.g., MVFC 440 and FCP 450, cf. FIG. 4). Sensors 1 and 2 share the same MVFC 740 and the model inputs from VMKS 730 outputs agree each other that are well constrained within the boundary of PVS responses 725 (cf. chart 720). The matching of curve 751 and 752 indicates consistency between the two sensors for predicting Methane concentration. Moreover, the consistency is maintained during an extensive period of time, and a wide range of values of Methane concentration.

Figure 8:
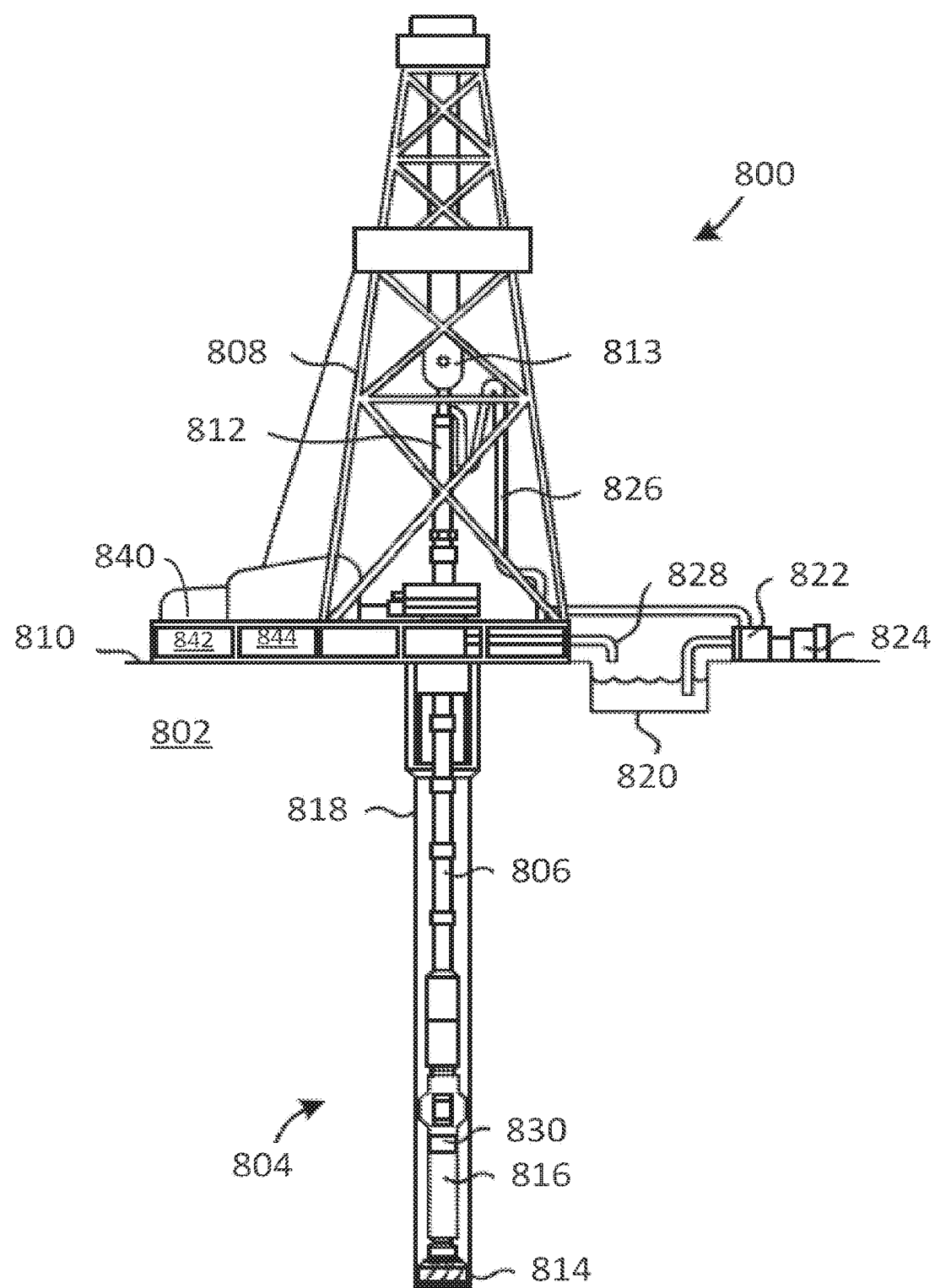
FIG. 8 is a drilling system configured to use a calibrated optical sensor for modifying a drilling parameter in measurement-while-drilling (MWD) and a logging-while-drilling (LWD) operations.

FIG. 8 is a drilling system 800 configured to use calibrated optical sensors installed on a downhole tool for modifying a drilling parameter, such as penetration rate or drilling direction, in a measurement-while-drilling (MWD) or a logging-while-drilling (LWD) operation, according to estimated wellbore or formation fluid properties. Boreholes may be created by drilling into the earth 802 using the drilling system 800. The drilling system 800 may be configured to drive a bottom hole assembly (BHA) 804 positioned or otherwise arranged at the bottom of a drill string 806 extended into the earth 802 from a derrick 808 arranged at the surface 810. The derrick 808 includes a kelly 812 and a traveling block 813 used to lower and raise the kelly 812 and the drill string 806.

The BHA 804 may include a drill bit 814 operatively coupled to a tool string 816 which may be moved axially within a drilled wellbore 818 as attached to the drill string 806. During operation, the drill bit 814 penetrates the earth 802 and thereby creates the wellbore 818. The BHA 804 provides directional control of the drill bit 814 as it advances into the earth 802. The tool string 816 can be semi-permanently mounted with various measurement tools (not shown) such as, but not limited to, measurement-while-drilling (MWD) and logging-while-drilling (LWD) tools, that may be configured to take downhole measurements of drilling conditions. In other embodiments, the measurement tools may be self-contained within the tool string 816, as shown.

Fluid or "mud" from a mud tank 820 may be pumped downhole using a mud pump 822 powered by an adjacent power source, such as a prime mover or motor 824. The mud may be pumped from the mud tank 820, through a stand pipe 826, which feeds the mud into the drill string 806 and conveys the same to the drill bit 814. The mud exits one or more nozzles arranged in the drill bit 814 and in the process cools the drill bit 814. After exiting the drill bit 814, the mud circulates back to the surface 810 via the annulus defined between the wellbore 818 and the drill string 806, and in the process, returns drill cuttings and debris to the surface. The cuttings and mud mixture are passed through a flow line 828 and are processed such that a cleaned mud is returned down hole through the stand pipe 826 once again.

The BHA 804 may further include a downhole tool 830 similar to the downhole tools described herein. More particularly, downhole tool 830 may have a calibrated optical sensor arranged therein, and the downhole tool 830 may have been calibrated prior to being introduced into the wellbore 818 using the sensor validation testing generally described herein. Moreover, prior to being introduced into the wellbore 818, downhole tool 830 may have been optimized by generally according to the steps illustrated in FIGS. 4, 5, 6, and 7. Downhole tool 830 may be controlled from the surface 810 by a computer 840 having a memory 842 and a processor 844. Accordingly, memory 842 may store commands that, when executed by processor 844, cause computer 840 to perform at least some steps in methods consistent with the present disclosure.

Figure 9:
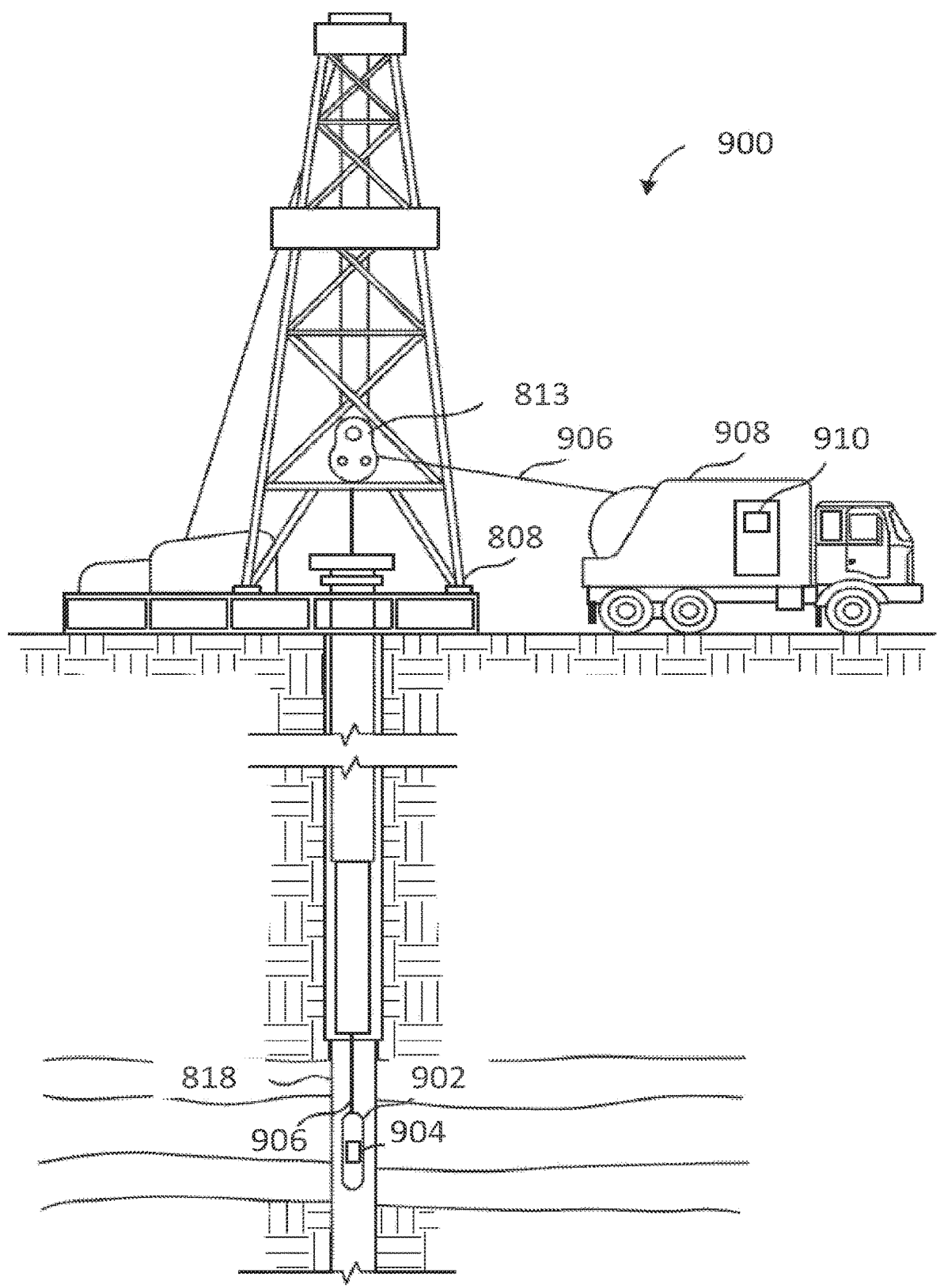
FIG. 9 is a wireline system configured to use a calibrated optical sensor during formation testing and sampling.

FIG. 9 illustrates a wireline system 900 that may employ one or more principles of the present disclosure. Wireline system 900 may be configured to use a formation tester and calibrated optical tool in determining types of formation fluids and the associated characteristics through sampling after drilling of wellbore 818 is complete. System 900 may include a downhole tool 902 that forms part of a wireline logging operation that can include one or more optical sensors 904, as described herein, as part of a downhole measurement tool. System 900 may include the derrick 808 that supports the traveling block 813. Wireline logging tool 902, such as a probe or sonde, may be lowered by wireline or logging cable 906 into the borehole 818. Tool 902 may be lowered to the potential production zone or the region of interest in the wellbore, and used in conjunction with other components of the formation tester such as packers and pumps to perform well testing and sampling. Sensor 904 may be configured to measure optical responses of the formation fluids, and any measurement data generated by downhole tool 902 and its associated optical sensors 904 can be real-time processed for decision-making, or communicated to a surface logging facility 908 for storage, processing, and/or analysis. Logging facility 908 may be provided with electronic equipment 910, including processors for various types of signal processing.

Figure 10:
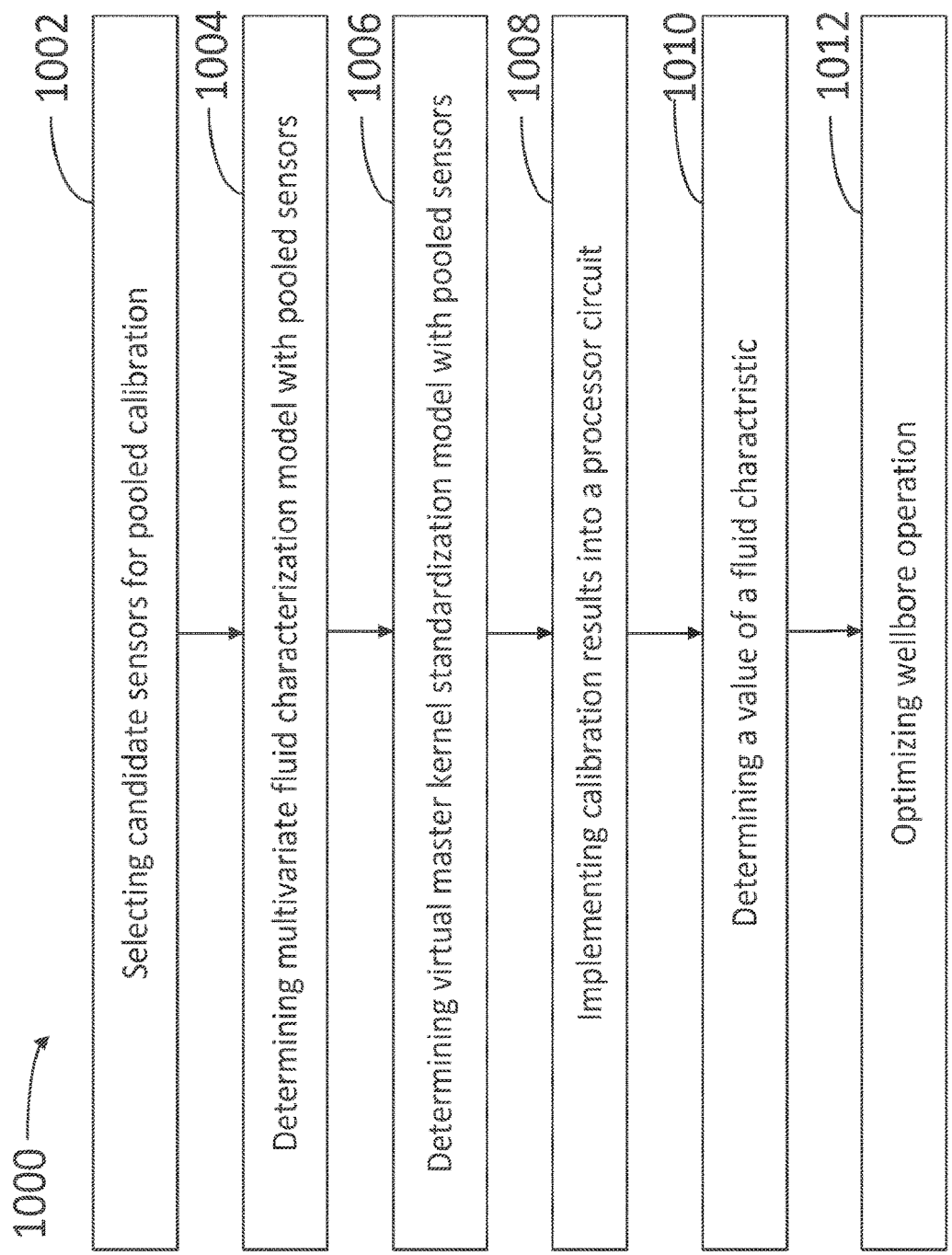
FIG. 10 illustrates a schematic flowchart of a method for optimizing well testing and sampling operation with a calibration module applied to pooled optical sensors for downhole fluid analysis as disclosed herein.

FIG. 10 illustrates a schematic flowchart of a method 1000 for optimizing wellbore operation with a calibration module applied to pooled optical sensors for downhole fluid analysis as disclosed herein. Method 1000 may be performed at least partially by a tool calibration system including a plurality of sensing elements for each sensor to be calibrated with a plurality of reference fluids (e.g., tool calibration system 100 and sensing elements 104, cf. FIG. 1) for determining a VMKS model (e.g., VMKS 430, cf. FIG. 4). In addition, method 1000 may also be implemented at least partially with a simulator to calculate synthetic optical sensor responses on a large collection of fluid samples in a standard oil library, and perform machine learning for determining multivariate fluid characterization algorithms with pooled synthetic sensors. Steps in method 1000 may be performed with a data analysis system coupled to a computer having a processor and a memory (e.g., data analysis system 134, computer 140, memory 142, and processor 144, or computer 840, memory 842, and processor 844, and logging tool 908, cf. FIGS. 1, 8 and 9). The data analysis system may perform at least some of the steps in method 1000 when the processor executes commands stored in the memory.

Methods consistent with the present disclosure may include at least some, but not all of the steps illustrated in method 1000, performed in a different sequence. Furthermore, methods consistent with the present disclosure may include at least two or more steps as in method 1000 performed overlapping in time, or almost simultaneously.

Step 1002 includes selecting candidate sensors for pooled calibration. In some embodiments, step 1002 includes collecting wheel spectra of candidate sensors in response to a light source, comparing the similarity of transmittance spectrum of each sensor element, and determining the final selection of sensors with spectral variation of each element within the specified tolerance. In some embodiments, wheel spectra based candidate sensor selection use PVS inputs from the pooled sensors (e.g., PVS responses 421, cf. FIG. 4). In some embodiments, step 1002 can be performed by comparing candidate real sensor responses on a plurality of reference fluids. The plurality of reference fluids may include at least one of a dead oil sample, a live oil sample, a natural gas sample, a water sample, a nitrogen containing sample, and a non-petroleum fluid including at least one of toluene, pentanediol, and dodecane. In some embodiments, step 1002 includes a reference fluids-based candidate sensor selection for calibration of a VMKS model using PRS inputs. In some embodiments, comparing candidate sensor responses on reference fluids includes collecting a laboratory data set and a simulated data set associated with the reference fluids, and matching the laboratory data and the simulated data to pre-determined sample temperatures and pressures.

Step 1002 may include finding potential candidate sensors that include sensing elements, such as ICEs, from the same design and formed in the same fabrication batch with similar controllable spectral variation. More generally, step 1002 may include selecting sensors having sensing elements with similar transmittance profiles, especially when the elements are made in different fabrication batches (e.g., transmittance spectra 521, cf. FIG. 5). For example, sensors with ICEs having similar optical transmittance spectra 521 (cf. FIG. 5) may be eligible for pooled calibration.

Step 1002 may include applying a principal component analysis (PCA) for selection of pooled sensor candidates. Accordingly, step 1002 may include applying PCA to a plurality of measured optical performance curves from each sensing element in the sensor over an effective wavelength range (e.g., transmittance spectra 521, cf. FIG. 5), and determining the best sensor candidates with maximized degree of matching on primary principal components of each sensing element.

Step 1004 includes determining a multivariate fluid characterization (MVFC) model with the pooled sensors (e.g., MVFC 440, cf. FIG. 4). In some embodiments, step 1004 includes simulating PVS responses on a large collection of fluid samples from a standard Optical-PVT database (e.g., synthetic parameter space in FIG. 2). Thus, step 1004 may include calculating the dot product of fluid spectroscopy data and the transmittance spectra of each sensor in the pool, to form a training data set with PVS responses as candidate inputs and known fluid compositions and properties as target outputs. Accordingly, step 1004 may include determining each MVFC model through neural network training using multi-input, single-output structure. In some embodiments, pooled sensors in step 1004 include a virtual master sensor featured with kernel sensor response (e.g., kernel sensor responses 425, calculated as the dot product of fluid spectroscopy data and kernel spectrum 525, cf. FIGS. 4 and 5) which is a mean of a plurality of pooled sensor responses on each corresponding sensing element. MVFC models determined from PVS responses as described above can adapt to a large signal variation from an imperfect reverse transformation in field data processing.

Step 1004 may include determining a plurality of MVFC models for estimation of each fluid composition and property. Accordingly, the plurality of MVFC models may form a network committee consisting of a number of candidate neural networks using different sets of optical inputs. These member networks can be implemented into real-time prediction software to provide averaged ensemble estimation for each fluid composition and property with statistical outlier removal. The candidate member networks can also be used in conjunction with an adaptive neuro-fuzzy inference system (ANFIS) in determining the best estimation of fluid answer products.

Step 1006 includes determining a virtual master kernel standardization (VMKS) model using pooled sensor calibration for transforming optical sensor data from tool parameter space to synthetic parameter space (e.g., reverse transformation 203, cf. FIG. 2, and VMKS 430, cf. FIG. 4).

Step 1006 may include collecting calibration data on reference fluids for each sensor in the pool, forming combined training data set using PRS responses as inputs and simulated kernel responses of the virtual master sensor on the same reference fluids as target outputs at matched temperatures and pressures. Further, step 1006 may include training a MIMO neural network to determine the VMKS model. Further, step 1006 may be collaboratively used with step 1004 to better tolerate noisy data and minimize the impact of imperfect data transformation on fluid characterization through kernel mapping and expanding calibration data range with pooled sensor inputs. Step 1006 may include calibrating the VMKS model as a neural network "committee" consisting of a number of member networks with different structures, and the committee model output can be averaged over the member network outputs to minimize the uncertainty of optical data transformation.

Step 1008 includes implementing the pooled sensor calibration results into a processor circuit as a unit of optical tool. All VMKS and MVFC model coefficients can be written to a calibration file, and applied with a software processor when optical sensor measurement data are received. The processor circuit may be as processor 144 (cf. FIG. 1). The processor circuit may also be implemented with other algorithms, such as ANFIS, which can be used in conjunction with neural network based models for complicated downhole fluid analysis.

Step 1010 includes determining a value of a fluid characteristic by applying the multivariate fluid characterization models. The MVFC models receive synthetic optical sensor responses to the fluid sample as inputs. Accordingly, the synthetic sensor responses are transformed from operational sensor responses using the virtual master kernel standardization models. In some embodiments, step 1010 includes performing real-time fluid analysis using hardware and software units. The hardware may include a sensing platform (e.g., sensing platform 122), and the data analysis system including the processor and the memory circuits. The software may include a plurality of commands and instructions stored in the memory circuit. The fluid in step 1010 may include a sample fluid, a reference fluid, or a formation fluid in a wellbore operation.

Step 1012 includes optimizing a wellbore operation based on the real-time fluid analysis. In some embodiments, a wellbore operation is a formation sampling and testing performed using a wireline formation tester with a dual-sensor optical tool attached to the tool string. Accordingly, each sensor in the dual-sensor tool may share MVFC and VMKS models. Step 1012 includes determining an appropriate time for collecting a representative fluid sample. For example, it may be desirable to collect a sample with minimized contamination level based on real-time estimated FCP and the consistency of prediction with each operational sensor.

Step 1012 may include applying candidate MVFC models to estimate fluid density with optical sensor inputs, and comparing the prediction with actual density measurement from a non-optical and high-resolution density sensor installed on flow line. The degree of matching may indicate the uncertainty of VMKS and MVFC models and help determine if default real-time fluid predictive models need to be adjusted with other candidate models, using additional input from density sensor for example, or if a second processor, such as ANFIS processor, is needed to re-estimate a particular high-uncertainty fluid composition or property for early decision making.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of I, II, and III" or "at least one of I, II, or III" each refer to only I, only II, or only III; any combination of I, II, and III; and/or at least one of each of I, II, and III.

Embodiments disclosed herein include:

A. A method including selecting candidate sensors for pooled calibration and thereby obtaining pooled sensors. The method also includes determining a multivariate fluid characterization model with the pooled sensors and determining a virtual master kernel standardization model with the pooled sensors. Further, the method includes implementing a calibration result into a processor circuit, and determining a value of a fluid characteristic by applying, in the processor circuit, the multivariate fluid composition model to a plurality of responses obtained from a plurality of sensor responses to the fluid sample. The plurality of responses is obtained from the plurality of sensor responses using the virtual master kernel standardization model. The method also includes optimizing a wellbore operation based on the value of the fluid characteristic.

B. A device including an optic cell that provides a location where a sample fluid interacts with an illumination light to produce an interacted light and a plurality of sensing elements disposed on a sensing platform, each sensing element receiving the interacted light and generating a computation light. The devices also includes a detector that receives and measures the computation light from each sensing element and a fluid analysis system that receives a signal from the detector indicative of a measurement of the computation light. The signal from the detector comprises a plurality of signals and each signal is associated with one of the plurality of sensing elements. The device may further include a processor included in the fluid analysis system to perform a multivariate fluid characteristic operation to the plurality of signals and thereby obtain a fluid characteristic value from the multivariate fluid characteristic operation. The fluid analysis system modifies a wellbore operation based on the fluid characteristic value.

C. A non-transitory, computer readable medium storing commands which, when executed by a processor, cause a computer to select candidate sensors for pooled calibration and thereby obtain pooled sensors and determine a multivariate fluid characterization model with the pooled sensors. The commands may also cause the computer to determine a virtual master kernel standardization model with the pooled sensors and implement a calibration result into a processor circuit, perform a real-time fluid analysis by using the processor circuit, and optimize a wellbore operation based on the real-time fluid analysis. In some embodiments, selecting candidate sensors for pooled calibration includes collecting a response data using the selected candidate sensors with a plurality of reference fluids.

Each of embodiments A, B, and C may have one or more of the following additional elements in any combination. Element 1, wherein the plurality of responses obtained from a plurality of sensor responses includes a plurality of responses in the synthetic parameter space associated with the pooled sensors. Element 2, wherein determining the virtual master kernel standardization model with the pooled sensors includes forming a training data set from reference fluids using measured responses from a plurality of sensing elements as inputs and a plurality of simulated kernel responses from a virtual master sensor as outputs for training a multi-input, multi-output neural network. Element 3, wherein determining the multivariate fluid characterization model with the pooled sensors includes forming a training data set from a plurality of fluid samples using synthetic responses of a plurality of sensing elements as inputs and a known fluid composition or property as output for training a multi-input, single-output neural network. Element 4, wherein selecting candidate sensors for pooled calibration of a multivariate fluid characterization model includes performing a principal component analysis to a plurality of measured optical performance curves from a sensing element in each candidate sensor. Element 5, wherein selecting candidate sensors for pooled calibration of a virtual master kernel standardization model includes collecting a sensor response using selected candidate sensors to measure a plurality of reference fluids, wherein the plurality of reference fluids includes at least one of a dead oil sample, a live oil sample, a natural gas sample, a water sample, a nitrogen containing sample, and a non-petroleum fluid including at least one of toluene, pentanediol, and dodecane. Element 6, wherein selecting candidate sensors for pooled calibration of a virtual master kernel standardization model further includes collecting an actual sensor response from a laboratory data and a simulated virtual master kernel sensor data associated with a reference fluid, and matching the laboratory data and the simulated data to a pre-determined sample temperature and a pre-determined sample pressure. Element 7 wherein determining a multivariate fluid characterization model includes modeling a fluid composition and property related predictive algorithm with a plurality of sensors to be used on the same or different tools using a nonlinear multi-input, single-output neural network. Element 8, wherein determining a virtual master kernel standardization model includes modeling an optical data transformation algorithm with a plurality of sensors to be used on the same or different tools using a nonlinear multi-input, multi-output neural network. Element 9, wherein optimizing the wellbore operation includes determining a time for collecting a sample where the contamination level is minimal. Element 10, wherein optimizing the wellbore operation includes evaluating model performance and adjusting candidate model selection based on a degree of matching between measured fluid density from a non-optical sensor and the estimated fluid density from a plurality of candidate multivariate density predictive models using a plurality of optical sensor inputs.

Element 11, wherein at least one of the plurality of sensing elements includes an integrated computational element. Element 12, wherein the multivariate fluid characteristic operation includes a trained neural network having commands stored in a memory and executed in a processor, the memory and the processor being included in the fluid analysis system. Element 13, wherein the sensing platform provides at least a portion of the interacted light having similar optical properties to each of the plurality of sensing elements. Element 14, wherein the sensing platform provides the same portion of the interacted light to the plurality of sensing elements in a time sequence. Element 15, wherein the sensing platform comprises a rotary wheel having the sensing elements radially disposed on the plane of the wheel, and the rotary wheel rotates about an axis parallel to an optical beam including the interacted light.

Element 16, wherein the commands to cause the computer to determine the virtual master kernel standardization model include commands to model a cross-tool optical data transformation with a nonlinear multi-input, multi-output neural network. Element 17, wherein the commands to cause the computer to select candidate sensors for pooled calibration include commands to cause the computer to perform a principal component analysis to a plurality of measured optical performance curves from a sensing element in each candidate sensor. Element 18, wherein the commands to cause the computer to select candidate sensors for pooled calibration include commands to cause the computer to collect a sensor response using the selected candidate sensors to measure a plurality of reference fluids, wherein the plurality of reference fluids comprises at least one of a dead oil sample, a live oil sample, a natural gas sample, a water sample, a nitrogen containing sample, and a non-petroleum fluid including at least one of toluene, pentanediol, and dodecane. Element 19, wherein the commands to cause the computer to select candidate sensors for pooled calibration include commands to cause the computer to collect a sensor response from a laboratory data or a simulated data associated with a reference fluid, and matching the laboratory data or the simulated data to a pre-determined sample temperature and a pre-determined sample pressure.

By way of non-limiting example, exemplary combinations applicable to embodiments A, B, and C include: Element 1 with Element 2; Element 11 with Element 12, and Element 18 with Element 19.

What is claimed is:

1. A method, comprising:
   selecting candidate sensors for pooled calibration, thereby obtaining pooled sensors;
   determining a multivariate fluid characterization model using virtual sensor responses corresponding to the pooled sensors;
   determining a virtual master kernel standardization model using real sensor responses of the pooled sensors as inputs;
   implementing a calibration result that includes the multivariate fluid characterization model and the virtual master kernel standardization model into a processor circuit; and
   determining a value of a fluid characteristic by applying, in the processor circuit, the multivariate fluid characterization model to a plurality of virtual sensor responses obtained from a plurality of real sensor responses to the fluid sample, wherein the plurality of virtual sensor responses is obtained from the plurality of real sensor responses using the virtual master kernel standardization model.

2. The method of claim 1, wherein the plurality of virtual sensor responses obtained from a plurality of real sensor responses in determining a value of a fluid characteristic comprises a plurality of responses in a synthetic parameter space associated with the pooled sensors.

3. The method of claim 1, wherein determining the virtual master kernel standardization model comprises forming a training data set of pooled real sensor responses to reference fluids from a plurality of sensing elements as inputs and a plurality of simulated kernel responses from a virtual master sensor as outputs for training a multi-input, multi-output neural network.

4. The method of claim 1, wherein determining the multivariate fluid characterization model with the pooled sensors comprises forming a training data set from a plurality of fluid samples using synthetic responses of a plurality of sensing elements as inputs and a known fluid composition or property as output for training a multi-input, single-output neural network.

5. The method of claim 1, wherein selecting candidate sensors for pooled calibration of a multivariate fluid characterization model comprises applying a principal component analysis to a plurality of measured optical performance curves for a sensing element in each candidate sensor.

6. The method of claim 1, wherein selecting candidate sensors for pooled calibration of a virtual master kernel standardization model comprises collecting a sensor response using selected candidate sensors to measure a plurality of reference fluids, wherein the plurality of reference fluids comprises at least one of a dead oil sample, a live oil sample, a natural gas sample, a water sample, a nitrogen containing sample, and a non-petroleum fluid including at least one of toluene, pentanediol, and dodecane.

7. The method of claim 1, wherein selecting candidate sensors for pooled calibration of a virtual master kernel standardization model further comprises:
   collecting an actual sensor response from a laboratory data and a simulated virtual master kernel sensor data associated with a reference fluid; and
   matching the laboratory data and the simulated data to a pre-determined sample temperature and a pre-determined sample pressure.

8. The method of claim 1, wherein determining a multivariate fluid characterization model comprises modeling a fluid composition or property using a nonlinear multi-input, single-output neural network.

9. The method of claim 1, wherein determining a virtual master kernel standardization model comprises modeling an optical data transformation algorithm with a plurality of sensors to be used on the same or different tools using a nonlinear multi-input, multi-output neural network.

10. The method of claim 1, further comprising optimizing a wellbore operation based on the value of the fluid characteristic, wherein optimizing the wellbore operation comprises determining a time for collecting a sample.

11. The method of claim 1, further comprising optimizing a wellbore operation based on the value of the fluid characteristic wherein optimizing the wellbore operation comprises evaluating model performance and adjusting candidate model selection based on a degree of matching between measured fluid density from a non-optical sensor and the estimated fluid density from a plurality of candidate multivariate density predictive models using a plurality of optical sensor inputs.

12. A non-transitory, computer readable medium storing commands which, when executed by a processor, cause a computer to:
   select candidate sensors for pooled calibration and thereby obtain pooled sensors;
   determine a multivariate fluid characterization model using virtual sensor responses corresponding to the pooled sensors;

determine a virtual master kernel standardization model using real sensor responses of the pooled sensors as inputs;

implement a calibration result that includes the multivariate fluid characterization model and the virtual master kernel standardization model into a processor circuit; and perform a fluid analysis by using the processor circuit including determining a value of a fluid characteristic by applying, in the processor circuit, the multivariate fluid characterization model to a plurality of virtual sensor responses obtained from a plurality of real sensor responses to the fluid sample, wherein the plurality of virtual sensor responses is obtained from the plurality of real sensor responses using the virtual master kernel standardization model.

13. The non-transitory, computer readable medium of claim 12, wherein the commands to cause the computer to determine the virtual master kernel standardization model comprise commands to model a cross-tool optical data transformation with a nonlinear multi-input, multi-output neural network.

14. The non-transitory, computer readable medium of claim 12, wherein the commands to cause the computer to select candidate sensors for pooled calibration comprise commands to cause the computer to apply a principal component analysis to a plurality of measured optical performance curves for a sensing element in each candidate sensor.

15. The non-transitory, computer readable medium of claim 12, wherein the commands to cause the computer to select candidate sensors for pooled calibration comprise commands to cause the computer to collect a sensor response using the selected candidate sensors to measure a plurality of reference fluids, wherein the plurality of reference fluids comprises at least one of a dead oil sample, a live oil sample, a natural gas sample, a water sample, a nitrogen containing sample, and a non-petroleum fluid including at least one of toluene, pentanediol, and dodecane.

16. The non-transitory, computer readable medium of claim 12, wherein the commands to cause the computer to select candidate sensors for pooled calibration comprise commands to cause the computer to collect a sensor response from a laboratory data or a simulated data associated with a reference fluid, and matching the laboratory data or the simulated data to a pre-determined sample temperature and a pre-determined sample pressure.

* * * * *